United States Patent
Müller et al.

(10) Patent No.: US 8,034,562 B2
(45) Date of Patent: Oct. 11, 2011

(54) METHOD FOR OBTAINING PLASMID-DNA BY MEANS OF AN AQUEOUS BIPHASIC SYSTEM

(75) Inventors: Markus Müller, Dormagen-Nievenheim (DE); Jürgen Hubbuch, Köln (DE); Andreas Frerix, Kalker-Kehrum (DE); Maria-Regina Kula, München (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 10/558,326

(22) PCT Filed: May 28, 2004

(86) PCT No.: PCT/EP2004/005799
§ 371 (c)(1),
(2), (4) Date: Dec. 27, 2005

(87) PCT Pub. No.: WO2004/106516
PCT Pub. Date: Dec. 9, 2004

(65) Prior Publication Data
US 2006/0286080 A1 Dec. 21, 2006

(30) Foreign Application Priority Data
May 28, 2003 (DE) .................................. 103 24 511

(51) Int. Cl.
*C12Q 1/68* (2006.01)
(52) U.S. Cl. ........................................................ 435/6.1
(58) Field of Classification Search ................. 435/91.1, 435/91.2, 6, 6.1
See application file for complete search history.

(56) References Cited

FOREIGN PATENT DOCUMENTS
GB 2333526 7/1999

OTHER PUBLICATIONS

Datar et al. Journal of Biotechnology, vol. 3, pp. 207-219 (1986).*
Hatti-Kaul. Aqueous two-phase systems, Molecular Biotechnology, vol. 19, pp. 269-277, 2001.*
Michael Buchmeiser, Polymeric Materials in Organic Synthesis and Catalysis, WILEY-VCH, ISBN 3-527-30630-7, p. 245, 2003.*
Cole, *Biotechniques*., 11(1): 18, 20, 22-24, (1991).
Prazeres et al., *Trends in Biotechnology*, 17(4): 169-174 (1999).
Ribeiro et al., *Biotechnol. Bioeng.*, 78(4): 376-384 (2002).

* cited by examiner

*Primary Examiner* — Samuel Woolwine
*Assistant Examiner* — Cynthia Wilder
(74) *Attorney, Agent, or Firm* — Fanelli Haag PLLC

(57) ABSTRACT

The invention relates to a process for isolation of plasmid DNA from biomass by means of an aqueous 2-phase system having a polymer component and a salt component, characterized in that the resuspension of the biomass employed, the alkaline lysis of the biomass, the neutralization of the alkaline lysis batch and the separation of the plasmid DNA from the contaminants are carried out in a single reaction vessel (one-pot process) rendered possible in that the neutralization of the alkaline lysis batch is carried out in one and the same container by addition of potassium phosphate and one component of the aqueous 2-phase system is therefore already present. The second component of the aqueous 2-phase system is a PEG having a molecular weight of the mathematical average of about 600 g/mol to 1,000 g/mol.

39 Claims, 1 Drawing Sheet

METHOD FOR OBTAINING PLASMID-DNA BY MEANS OF AN AQUEOUS BIPHASIC SYSTEM

This application is a United States national stage filing under 35 U.S.C. §371 of international (PCT) application No. PCT/EP2004/005799, filed May 28, 2004 and designating the US, which claims priority to German application 103 24 511.1, filed May 28, 2003.

The invention relates to a simplified process, which is shorter in time, for isolation of plasmid DNA from biomass, such as e.g. bacteria, by means of an aqueous 2-phase system having a polymer component and a salt component, and to the use of the plasmid DNA obtained in this way in gene therapy and in genetic vaccination. The invention furthermore relates to a kit for carrying out the process.

One of the possibilities of isolating plasmid DNA from biomass is lysis of the biomass and subsequent separation of the clarified lysates from the biomass in an aqueous 2-phase system. The Dutch microbiologist Beijerinck already discovered in 1896 that after mixing agar and soluble starch in water, two aqueous phases form after some time. This property of some polymers was rediscovered and pursued by Per Albertson in about 1960. He recognized the potential of such a system for purification of viruses, cells and also cell constituents. Due to the high water content of the biocompatible medium and the stabilizing properties of the phase components, such phase systems are correspondingly particularly suitable for purification of sensitive biomolecules. Aqueous 2-phase systems are obtained either by addition of two different polymers (polymer/polymer system; e.g. polyethylene glycol (PEG) and dextran), or by a polymer (e.g. polyethylene glycol) and a highly concentrated salt (e.g. citrates, sulphates or phosphates).

The widely used techniques for the preparation of recombinant DNA and the ever increasing interest in gene therapy for treatment of the most diverse diseases and genetic vaccination have caused the demand for a process for the purification of plasmid DNA which can also be used on an industrial scale to increase. Alternative methods, such as centrifugation in a caesium chloride (CsCl) density gradient or phenol extraction, are thus inconceivable for a plasmid DNA obtained for therapeutic use because of the toxicity of the substances, in the same way as the amount of toxic or combustible substances to be employed for a production on an industrial scale.

The prior art also includes processes for isolation of plasmid DNA in which aqueous 2-phase systems having a salt component and a polymer component are used. Cole (Biotechniques. July 1991; 11(1):18, 20, 22-24) published an aqueous 2-phase system for isolation of plasmids using PEG as the polymer component and e.g. ammonium sulphate or sodium dihydrogen phosphate as the salt component. The isolation of the plasmid pTZ 18U from $E.\ coli$ DH5a is described concretely. The corresponding cell pellet was broken down by means of a lysis buffer comprising SDS and NaOH. The lysate was introduced into an appropriate phase-forming system and the mixture was mixed and then centrifuged. This was repeated twice more with the lower phase and a fresh upper phase containing no lysate. The lower phase was then dialysed against a Tris/EDTA buffer and the plasmid was finally isolated in this way.

Ribeiro et al. (Biotechnol. Bioeng. May 20, 2002; 78(4): 376-84) furthermore describe an aqueous 2-phase system with PEG as the polymer component and dipotassium hydrogen phosphate ($K_2HPO_4$) as the salt component. The isolation of the plasmid pCF1-CFTR from $E.\ coli$ DH5a is reported. For this, the cells were first broken down by means of alkaline lysis (lysis buffer containing NaOH and SDS) and the lysate was then neutralized with 3 M sodium acetate. The cell debris, proteins and genomic DNA (gDNA) were subsequently removed by centrifugation of the batch. The clarified lysate was employed in the abovementioned aqueous 2-phase system. However, this process has the disadvantages that it is very expensive in terms of apparatus and time. Last but not least, the reason for the time consumed is that a lysis of the biomass is first carried out in a separate batch in this system and more than one reaction vessel is therefore necessary for such a process.

The present invention is intended to overcome the disadvantages of the processes known from the prior art, and in particular the object of the invention is simplification and shortening in the time of the processes known from the prior art for isolation of plasmid DNA from biomass. In addition, the object of the present invention is to provide a process which can be carried out not only on a laboratory scale but also on an industrial scale and with which e.g. plasmid DNA for clinical use in gene therapy or genetic vaccination can be prepared. A further object of the present invention is to provide a process which can easily be automated.

The object is achieved according to the invention by a process for isolation of plasmid DNA from biomass by means of an aqueous 2-phase system having a polymer component and a salt component, characterized in that the resuspension of the biomass employed, the alkaline lysis of the biomass, the neutralization of the alkaline lysis batch and the separation of the plasmid DNA from the contaminants (such as e.g. cell debris, RNA and gDNA) are carried out in a single reaction vessel (one-pot process). This is rendered possible according to the invention in that the neutralization of the alkaline lysis batch is carried out in one and the same container by addition of potassium phosphate and one component of the aqueous 2-phase system is therefore already present, and in that the second component of the aqueous 2-phase system is a PEG having a molecular weight of the mathematical average of about 600 g/mol to 1,000 g/mol, but is preferably formed by a mixture of PEG 600 and PEG 1000.

The process according to the invention comprises the following steps:
 a) resuspension of the biomass,
 b) addition of lysis buffer, incubation for a sufficiently long period of time for lysis of the biomass,
 c) addition of the salt component, incubation for a sufficiently long period of time,
 d) addition of the polymer component, thorough mixing of the solution, awaiting of the formation of phases.

Because of the simplicity due to the one-pot process, the process according to the invention is advantageously an automatable process for isolation of plasmid DNA. There is an ever increasing demand for automatability of such processes on a relatively small scale, e.g. for rapid identification of clones. However, such an automatability can be realized only with difficulty with the known 2-phase systems. Only with the process according to the invention can such an automation be easily achieved.

The process claimed can also advantageously be employed for the production of plasmid DNA on an industrial scale. The reason for this lies in the simplicity, the low expenditure on apparatus and the use of non-toxic and inexpensive components.

One of the features of this process which are essential to the invention is that the resuspension of the biomass employed, the alkaline lysis of the biomass, the neutralization of the lysis batch and the separation of the plasmid DNA from the contaminants take place in an aqueous 2-phase system successively in a single container, that is to say as a one-pot process, without there being an intermediate centrifugation step with subsequent separating off of a precipitate. The process according to the invention is greatly simplified by this means, is significantly less expensive in terms of apparatus, and is greatly shorter in time compared with the processes known from the prior art.

The process according to the invention uses a 2-phase system of a polymer component and a salt component. This has the advantage that the salts used are relatively inexpensive compared with a second polymer component (e.g. dextran) in a 2-phase system having two different polymer components.

In the case of the present invention, the term "plasmid DNA" also includes, in addition to plasmids, cosmids as well as phasmids, and also eukaryotic vectors, such as e.g. yeast vectors, such as, for example, yeast artificial chromosomes (YACs) and similar structures. In the context of the present invention, the term "biomass" includes all life forms which are capable of carrying and multiplying or passing on to their descendants this plasmid DNA, such as e.g. bacteria, yeasts etc.

The biomass which carries the plasmid DNA is obtained in this context by centrifugation of an appropriate incubation batch or any other suitable method for concentrating the biomass. The person skilled in the art is familiar with such methods and how to carry them out. The resuspension of the biomass, e.g. of the bacteria pellet, and the alkaline lysis of the biomass subsequently likewise proceed in a manner and way known to the person skilled in the art, e.g. by means of the commercially obtainable QIAGEN Plasmid Kits and the resuspension buffer P1 and lysis buffer P2 contained therein (QIAGEN, Hilden, Germany) or other suitable buffers, in a container which seems suitable to the person skilled in the art. Up the this point the procedure is conventionally in accordance with the particular known instructions. The lysis buffer preferably contains sodium dodecyl sulphate (SDS) as one of the components.

Advantageously and surprisingly, the lysis of the biomass and the lysate during and after addition of the salt component can furthermore also be carried out under agitation of the lysis batch or lysate, such as vigorous shaking and/or stirring or the like. The processes known from the prior art have the disadvantage that the gDNA fragments necessarily formed by shearing forces during such a treatment of the lysis batch or lysate cannot be separated to a satisfactory degree from the plasmid DNA to be isolated. Such a treatment of the lysis batch or lysate is therefore usually avoided by the person skilled in the art. In the aqueous 2-phase system according to the invention, however, the gDNA fragments formed in this way are also separated off from the plasmid DNA. This results on the one hand in a lower susceptibility of the system towards contamination of the plasmid DNA by gDNA, and furthermore agitation of the lysis batch, such as e.g. vigorous stirring, shaking or the like, additionally advantageously increases the release of the plasmid DNA from the biomass, and the agitation of the lysate, such as e.g. vigorous stirring, shaking or the like, during and/or after addition of the salt component according to the invention additionally advantageously increases the release of the plasmid DNA from the precipitate agglomerates which form, which leads to a significant increase in the yield of plasmid DNA. In a preferred embodiment, the gDNA sheared by agitation of the lysis batch or lysate is removed from the plasmid DNA to the extent of >90%, particularly preferably to the extent of >95% and very particularly preferably to the extent of >99%, compared with the otherwise conventional potassium acetate precipitation after the lysis.

The substances which are conventional for the person skilled in the art, such as e.g. potassium acetate, are not resorted to for neutralization of the batch of the alkaline lysis and for precipitation of the proteins. According to the invention, the alkaline lysis batch is advantageously neutralized with the salt component according to the invention. The salt component in the context of the invention is potassium phosphate, by which is understood, according to the invention, tripotassium phosphate ($K_3PO_4$), dipotassium hydrogen phosphate ($K_2HPO_4$) and/or potassium dihydrogen phosphate ($KH_2PO_4$). Preferably, exclusively one of these or a mixture of these potassium phosphates is added to the alkaline lysis batch. $K_2HPO_4$ and/or $KH_2PO_4$ is particularly preferably used. If SDS is used in the lysis buffer, the process according to the invention furthermore renders possible the precipitation of proteins out of the lysis batch in the form of potassium dodecyl sulphate (PDS)-protein complexes.

According to the invention, the salt component is employed such that a 2-phase system forms together with one of the polymer component compositions and concentrations according to the invention, but the concentration of the salt component at which the plasmid DNA changes from the lower phase (salt phase), in which it is at lower concentrations, into the upper phase (polymer phase) not being exceeded, and contaminants, such as RNA and gDNA, remaining in the upper phase or in the interphase. It is well-known that 2-phase systems occur only when limiting concentrations are exceeded. The course of such limiting concentrations can be plotted in a phase diagram. This is easy to achieve for the person skilled in the art.

In a preferred embodiment of the process according to the invention, the depletion of the RNA contaminants from the plasmid DNA is >80%, compared with the potassium acetate precipitation conventionally used after lysis of the biomass, the depletion in the RNA contaminants is particularly preferably >85% and the depletion in the RNA contaminants is very particularly preferably >90%.

For the process according to the invention, the potassium phosphate is preferably added in the form of a buffer. In this context, the buffer particularly preferably contains a mixture of $K_2HPO_4$ and $KH_2PO_4$. The buffers according to the invention are employed with a pH in the range of from pH 5.8 to pH 8.5 and preferably with a pH in the range of from pH 6.5 to pH 8. For example, a composition of 3.83 M $K_2HPO_4$ and 2.45 M $KH_2PO_4$ (a pH of approx. 7 results) can particularly preferably be used in the process according to the invention. In this context, $K_2HPO_4$ and $KH_2PO_4$ are employed in a total concentration, based on the 2-phase system, of 5-30% (w/w), preferably in a total concentration of 10-25% (w/w) and particularly preferably in a total concentration of 20% (w/w). The potassium phosphate is usually added in a temperature range of between ice-cooled and room temperature. Room temperature in the context of the present invention designates a temperature range of from 18 to 25° C. An ice-cooled phosphate buffer is preferably employed in the process according to the invention. A long incubation time is advantageously not necessary after addition of the potassium phosphate, a thorough mixing of the solution which is as complete and uniform as possible, after the addition, is decisive. The incubation time is usually about 5 to 15 minutes. Preferably, as mentioned above, the batch is agitated, such as e.g. subjected to vigorous shaking, stirring or the like, during and/or after the addition of the salt component.

The polymer component in the context of the invention is PEG. A further essential feature of the process according to the invention is that polyethylene glycol having a molecular weight of the mathematical average of 600 to 1,000 g/mol, preferably of the mathematical average of 700-900 g/mol and particularly preferably of the mathematical average of 750-880 g/mol is employed as one of the two components of the 2-phase system. In the present invention, the PEG employed preferably comprises a mixture of polyethylene glycol having an average molecular weight of 600 g/mol (PEG 600) and polyethylene glycol having an average molecular weight of 1,000 g/mol (PEG 1000). Both PEGs are commercially obtainable (e.g. Fluka, Buchs, Switzerland). In this context, the ready-to-use PEG mixture comprises 30-50% (w/w) PEG 600 and 50-70% (w/w) PEG 1000, preferably 33-45% (w/w) PEG 600 and 55-67% (w/w) PEG 1000, particularly preferably 36-40% (w/w) PEG 600 and 60-64% (w/w) PEG 1000 and very particularly preferably 38% (w/w) PEG 600 and 62% (w/w) PEG 1000.

The concentration of the PEG in the aqueous 2-phase system according to the invention is chosen such that two phases are formed with the salt component, but the PEG concentration at which the plasmid DNAs change from the lower phase, in which they are at lower concentrations, into the upper phase not being exceeded. Preferably, however, the PEG content is at least 10% (w/w), and the upper limit is determined by the concentration of PEG at which the plasmid DNAs change from the lower phase, in which they are at lower concentrations, into the upper phase. After the addition of PEG, the solution should preferably have a temperature of from 10 to 50° C., particularly preferably a temperature of from 15 to 40° C. After formation of the phases, which takes some minutes to hours, depending on the volume of the batch, the plasmid DNA is in the salt-containing lower phase. The formation of the phases can optionally be accelerated by centrifugation of the batch, as a result of which there is advantageously a further shortening in the time of the process according to the invention. The conditions under which such a centrifugation step is carried out are familiar to the person skilled in the art.

Aqueous 2-phase systems have the advantage over phase systems which operate on the basis of matrices or other solid phases that they have a far higher capacity for the plasmid DNA to be purified, which is limited in practice only by the solubility in the phases. Furthermore, the dimensions of the process can be chosen virtually as desired because of the extremely simple apparatus. However, only with the simplifications claimed here can both an automation and, independently of this, a production on an industrial scale, for example for the production of more than 2 g plasmid DNA per lysis batch, be easily achieved. The plasmid DNA can also advantageously be freed from proteins, RNA and gDNA to a very high degree with the present invention. Plasmid DNA which is isolated by the process according to the invention can be employed without problems in gene therapy or genetic vaccination after a further purification step (for example via QIAGEN-Resin, QIAGEN, Hilden, Germany). Thus, large amounts of highly pure plasmid DNA can advantageously be produced with a very low expenditure on apparatus using non-toxic substances and with comparatively low costs being incurred. With regard to this it may be mentioned that the substances employed in the 2-phase system according to the invention, however, are acceptable e.g. compared with other isolation methods, such as e.g. CsCl density gradient centrifugation or phenol extraction, and can be removed completely and easily from the purified plasmid DNA.

One of the great advantages of the process according to the invention is that, surprisingly, there is a depletion in the open circular plasmid DNA (ocDNA) from the plasmid DNA to be isolated. The plasmid DNA isolated with the process according to the invention has, compared with plasmid DNA which has been isolated with processes known from the prior art, a lower content of the ocDNA contaminants in comparison with the preferred supercoiled form (scDNA). This process thus shows a selectivity for separation of plasmid topoisomers, that is to say of ocDNA and scDNA. Precisely this separation of the plasmid topoisomers and the depletion of the gDNA already mentioned are of great importance in particular in an isolation of plasmid DNA on an industrial scale and during subsequent clinical use of the plasmid DNA in some applications, and are not to be achieved to a satisfactory degree with the processes to date for isolation of plasmid DNA.

In a further embodiment of the process according to the invention, the lower phase containing the plasmid DNA forming in step d) is separated from the upper phase containing the contaminants. The lower phase is then set up again for the formation of a 2-phase system by addition of the salt component in the form which results in a concentration of the salt component according to step c), and then by addition of the polymer component according to step d). In this repetition of the last part of the process according to the invention, after the addition of the polymer component the mixture is mixed thoroughly again and the formation of phases is awaited. Here also, the plasmid DNA is in the lower phase. This step can optionally be carried out once or in a number of times which seem appropriate to the person skilled in the art. Carrying out this optional step leads to a repeated purification of the plasmid DNA and therefore to a further depletion of contaminants, such as e.g. RNA, from the plasmid DNA. The additional purification step(s) comprise(s) the following steps:

e) separation of the lower phase forming in step d) from the upper phase formed in step d) and containing the contaminants, f) addition of the salt component in the form which results in a concentration of the salt component according to step c), g) renewed addition of the polymer component according to step d), h) thorough mixing of the solution, awaiting of the formation of phases.

After the process according to the invention, the plasmid DNA must still be obtained from the lower phase formed in step d). The isolation and desalination of the plasmid DNA from the lower phase formed in step d) are conventionally carried out by ultrafiltration/diafiltration. However, any further method of isolation and/or desalination of the plasmid DNA from the lower phase which seems appropriate to the person skilled in the art may also be used in the context of the present invention.

In an alternative embodiment, instead of the biomass, a clarified lysate which contains the plasmid DNA to be isolated can also be employed as the starting material in the process according to the invention. In this embodiment of the invention, the lysis step is of course omitted, or a clarification of the lysate additionally takes place after the lysis step. All the methods which seem suitable to the person skilled in the art can be used for the preparation of a clarified lysate. A conventional method in the prior art is clarification of the lysate by precipitation with potassium acetate and subsequent centrifugation of the mixture to separate off the precipitate formed. For this case, potassium phosphate corresponding to the above statements is first added to the clarified lysate, and PEG is then added according to the invention. All further steps are identical to the process according to the invention in which biomass is employed as the starting point. If the precipitation step described above for clarification of the lysate is carried out with potassium phosphate, the PEG is added, as described, directly to the clarified lysate. All further steps are identical to the process according to the invention in which biomass is employed as the starting point. The experimental conditions which are required for a precipitation reaction as described above, both if potassium phosphate is used and if potassium acetate is used, are well-known to the person skilled in the art.

EXAMPLE 1

Figure 1:
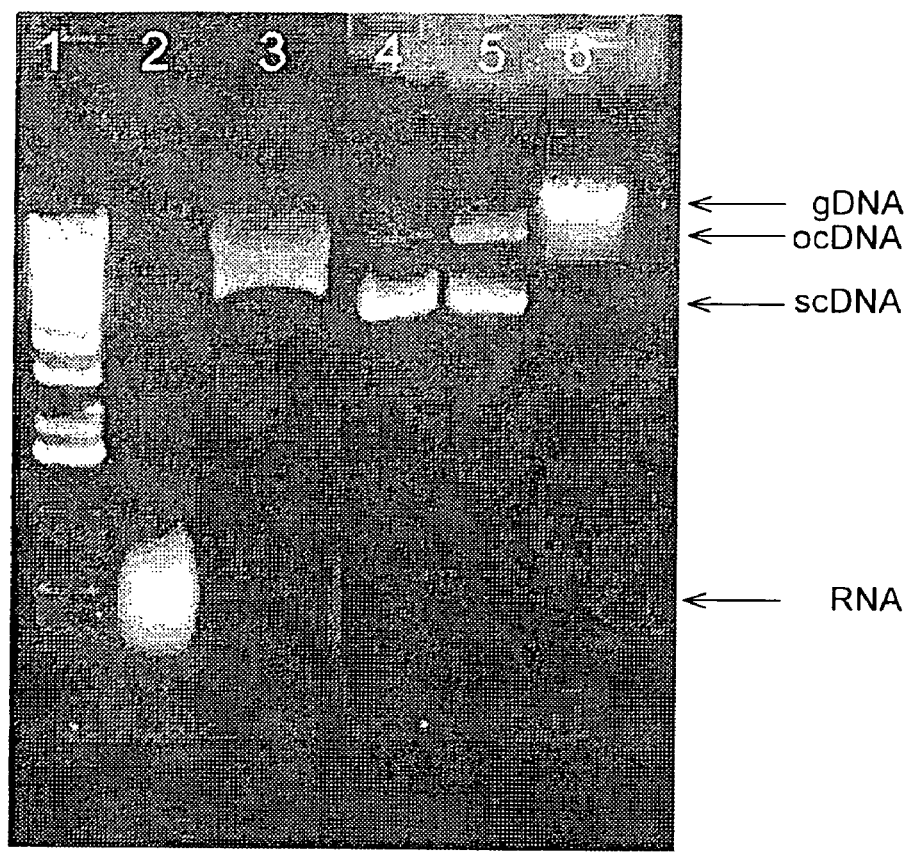
FIG. 1 shows the results of the isolation of pCMVβ from E. coli DH5a by the process according to the invention (see Example 1) in the form of a gel electrophoresis (0.8% agarose). A length standard can be seen in track 1. Track 2 shows the untreated upper phase, in which there is a massive amount of RNA. No plasmid DNA could be detected in the upper phase. Track 3 shows the untreated lower phase, in which the plasmid is highly concentrated (wide, blurred band), no RNA could be detected here. Track 4 shows the lower phase after desalination by means of ultrafiltration. Here also, only plasmid DNA can be detected, and the plasmid is mostly in the desired supercoiled form (scDNA), traces of open circular plasmid DNA (ocDNA) could also be detected. Track 5 shows a pCMVβ standard (18 µg/ml) and track 6 shows a gDNA standard (23 µg/ml).

Obtaining of pCMVβ from E. coli DH5a

For isolation of the plasmid pCMVβ, 0.6 g biomass from an overnight culture of E. coli DH5a (11 LB medium: 5 g/l yeast extract, 10 g/l tryptone, 85.6 mM NaCl) was obtained by centrifugation (5,000×g, 10 min, 4° C.). 6.9 ml resuspension buffer P1 (QIAGEN, Hilden, Germany) were added and the bacteria pellet was resuspended by vigorous shaking at room temperature. When the resuspension was complete, 7.5 ml lysis buffer P2 (QIAGEN, Hilden, Germany; room temperature) were added and the batch was mixed by inverting the vessel several times. After 5 min, $K_2HPO_4/KH_2PO_4$ buffer (2.5 g $KH_2PO_4$, 5 g $K_2HPO_4$, 7.5 ml $H_2O$; pH 7; ice-cooled) was added to the entire batch, the vessel was cautiously inverted and the batch was incubated on ice for 10 min. The entire batch was subsequently warmed to room temperature, PEG (2.137 g PEG 600, 3.488 g PEG 1000, 1.875 ml $H_2O$) was added and the batch was cautiously mixed. The phase separation took a few minutes.

No gDNA and no RNA could be detected in the lower phase by means of gel electrophoresis. The band of the plasmid DNA looks untypically wide and blurred in FIG. 1 (track 3) because of the high salt concentration in the lower-phase. Desalination of the lower phase by means of ultrafiltration (track 4) led to a correspondingly distinct band which virtually corresponds to the plasmid standard (track 5). Genomic DNA and proteins are to be found in the potassium dodecyl sulphate (PDS) flocculate and in the interphase.

EXAMPLE 2

Obtaining of pCMVβ from E. coli DH5a (20% PEG; 12% Phosphate)

For isolation of the plasmid pCMVβ, a 10% (w/w) biomass suspension (E. coli DH5a) in resuspension buffer P1 (QIAGEN, Hilden, Germany) was prepared by vigorous shaking at room temperature. When the resuspension was complete, 10 g of this batch were mixed with 10 ml lysis buffer P2 (QIAGEN, Hilden, Germany; room temperature) and the vessel was inverted several times. After 5 min, $K_2HPO_4/KH_2PO_4$ buffer (2 g $KH_2PO_4$; 4 g $K_2HPO_4$; 6 ml $H_2O$; pH 7.4; ice-cooled) was added to the entire batch and the batch was incubated on an overhead shaking machine at room temperature for 10 min. The entire batch was subsequently warmed to room temperature, PEG (3.8 g PEG 600; 6.2 g PEG 1000; 8.003 ml $H_2O$) was added and the batch was mixed on an overhead shaking machine at room temperature for a further 10 min. The phase separation was accelerated by centrifugation at 1,300×g for 5 min. The resulting lower phase had a volume of about 15 ml.

Analysis was carried out by means of HPLC (HP1090, Agilent, Waldbronn, Germany) and source 15PHE 4.6/100 (Amersham Bioscience, Freiburg, Germany) employing an $(NH_4)_2SO_4$ gradient. Detection was by absorption measurement at 260 nm. The following values were determined for the lower phase of the 2-phase system: 44 µg/ml plasmid DNA and 123 µg/ml RNA.

These values were compared with the values from a clarified lysate. For preparation of this clarified lysate, 1 ml of the 10% biomass suspension initially described was mixed with 1 ml lysis buffer P2 (QIAGEN, Hilden, Germany; room temperature) by inverting the vessel several times and the batch was incubated at room temperature for 5 min. 1 ml neutralization buffer P3 (QIAGEN, Hilden, Germany; ice-cooled) was then added and the batch was incubated on an overhead shaking machine at room temperature for 10 min. After centrifugation (5 min, 1,300×g, room temperature), the plasmid concentration and the RNA concentration in the supernatant (clarified lysate) were measured by means of HPLC. The biomass employed contained in the clarified lysate 710 µg plasmid DNA per g biomass and 11 mg RNA per g biomass.

Based on the starting values of the biomass in the clarified lysate, a 93% plasmid yield and an 83% RNA depletion result for the 2-phase system.

EXAMPLE 3

Obtaining of pCMVβ from E. coli DH5a (13% PEG; 16% Phosphate)

For isolation of the plasmid pCMVβ, a 10% (w/w) biomass suspension (E. coli DH5a) in resuspension buffer P1 (QIAGEN, Hilden, Germany) was prepared by vigorous shaking at room temperature. When the resuspension was complete, 10 g of this batch were mixed with 10 ml lysis buffer P2 (QIAGEN, Hilden, Germany; room temperature) and the vessel was inverted several times. After 5 min, $K_2HPO_4/KH_2PO_4$ buffer (2.666 g $KH_2PO_4$; 5.333 g $K_2HPO_4$; 8 ml $H_2O$; pH 7.4; ice-cooled) was added to the entire batch and the batch was incubated on an overhead shaking machine at room temperature for 10 min. The entire batch was subsequently warmed to room temperature, PEG (2.471 g PEG 600; 4.032 g PEG 1000; 7.498 ml $H_2O$) was added and the batch was mixed on an overhead shaking machine at room temperature for a further 10 min. The phase separation was accelerated by centrifugation at 1,300×g for 5 min. The resulting lower phase had a volume of about 25 ml.

Analysis was carried out by means of HPLC (HP1090, Agilent, Waldbronn, Germany) and source 15PHE 4.6/100 (Amersham Bioscience, Freiburg, Germany) employing an $(NH_4)_2SO_4$ gradient. Detection was by absorption measurement at 260 nm. The following values were determined for the lower phase of the 2-phase system: 28.4 µg/ml plasmid DNA and 187 µg/ml RNA.

These values were compared with the values from a clarified lysate. For preparation of this clarified lysate, 1 ml of the 10% biomass suspension initially described was mixed with 1 ml lysis buffer P2 (QIAGEN, Hilden, Germany; room temperature) by inverting the vessel several times and the batch was incubated at room temperature for 5 min. 1 ml neutralization buffer P3 (QIAGEN, Hilden, Germany; ice-cooled) was then added and the batch was incubated on an overhead shaking machine at room temperature for 10 min. After centrifugation (5 min, 1,300×g, room temperature), the plasmid concentration and the RNA concentration in the supernatant (clarified lysate) were measured by means of HPLC. The biomass employed contained in the clarified lysate 710 µg plasmid DNA per g biomass and 11 mg RNA per g biomass.

Based on the starting values of the biomass in the clarified lysate, a >99% plasmid yield and a 58% RNA depletion result for the 2-phase system.

EXAMPLE 4

Obtaining of pCMVβ from *E. coli* DH5a (30% PEG, 10% Phosphate)

For isolation of the plasmid pCMVβ, a 10% (w/w) biomass suspension (*E. coli* DH5a) in resuspension buffer P1 (QIAGEN, Hilden, Germany) was prepared by vigorous shaking at room temperature. When the resuspension was complete, 10 g of this batch were mixed with 10 ml lysis buffer P2 (QIAGEN, Hilden, Germany; room temperature) and the vessel was inverted several times. After 5 min, $K_2HPO_4/KH_2PO_4$ buffer (1.666 g $KH_2PO_4$; 3.333 g $K_2HPO_4$; 5 ml $H_2O$; pH 7.4; ice-cooled) was added to the entire batch and the batch was incubated on an overhead shaking machine at room temperature for 10 min. The entire batch was subsequently warmed to room temperature, PEG (5.7 g PEG 600; 9.3 g PEG 1000; 5 ml $H_2O$) was added and the batch was temperature-controlled in a water-bath at 40° C. for 15 min and with inversion of the vessel several times. The phase separation was accelerated by centrifugation at 1,300×g for 5 min. The resulting lower phase had a volume of about 11 ml.

Analysis was carried out by means of HPLC (HP1090, Agilent, Waldbronn, Germany) and source 15PHE 4.6/100 (Amersham Bioscience, Freiburg, Germany) employing an $(NH_4)_2SO_4$ gradient. Detection was by absorption measurement at 260 nm. The following values were determined for the lower phase: 61.8 µg/ml plasmid DNA and 173 µg/ml RNA.

These values were compared with the values from a clarified lysate. For preparation of this clarified lysate, 1 ml of the 10% biomass suspension initially described was mixed with 1 ml lysis buffer P2 (QIAGEN, Hilden, Germany; room temperature) by inverting the vessel several times and the batch was incubated at room temperature for 5 min. 1 ml neutralization buffer P3 (QIAGEN, Hilden, Germany; ice-cooled) was then added and the batch was incubated on an overhead shaking machine at room temperature for 10 min. After centrifugation (5 min, 1,300×g, room temperature), the plasmid concentration and the RNA concentration in the supernatant (clarified lysate) were measured by means of HPLC. The biomass employed contained in the clarified lysate 710 µg plasmid DNA per g biomass and 11 mg RNA per g biomass.

Based on the starting values of the biomass in the clarified lysate, a 96% plasmid yield and an 83% RNA depletion result for the 2-phase system.

EXAMPLE 5

Depletion of gDNA

A 20% biomass suspension was prepared by weighing out 4 g resuspension buffer P1 (QIAGEN, Hilden, Germany) and 1 g biomass (*E. coli* DH5a, containing no plasmid). This was broken down with ultrasound (Branson Sonifier 250, with converter type 102, settings: cycle 40%; intensity 4, 2 times 3 min) on ice. The gDNA was thereby released from the cell and subjected to severe shearing forces and fragmented. The batch was then centrifuged for 10 min at 5,000×g and 4° C. 300 µl lysis buffer P2 (QIAGEN, Hilden, Germany; room temperature) were then added to 300 µg of the supernatant and the batch was mixed. After 5 min, the entire batch was mixed with $K_2HPO_4/KH_2PO_4$ buffer (100 µg $KH_2PO_4$; 200 µg $K_2HPO_4$, 300 µl $H_2O$; pH 7.4; ice-cooled) and the batch was incubated on an overhead shaking machine at room temperature for 10 min. The entire batch was subsequently warmed to room temperature, PEG (85.5 µg PEG 600; 139.5 µg PEG 1000; 75 µl $H_2O$) was added and the batch was mixed on an overhead shaking machine at room temperature for a further 10 min. The phase separation was accelerated by centrifugation at 1,300×g for 5 min. The lower phase had a volume of about 0.75 ml.

Analysis was carried out by means of HPLC (HP1090, Agilent, Waldbronn, Germany) and source 15PHE 4.6/100 (Amersham Bioscience, Freiburg, Germany) employing an $(NH_4)_2SO_4$ gradient. Detection was by absorption measurement at 260 nm. The gDNA concentration in the supernatant of the breaking down operation (centrifugation after ultrasound treatment) was determined as 433 µg gDNA/ml. In the lower phase of the 2-phase system, a residual concentration of 1.7 µg gDNA/ml was determined by means of HPLC, which corresponds to a depletion of >99% of severely sheared gDNA.

The invention claimed is:
1. A method for isolating plasmid DNA from biomass, said method comprising an aqueous 2-phase system having a polymer component and a salt component, said method comprising the steps of:
   (a) suspending the biomass,
   (b) adding alkaline lysis buffer and incubating for a sufficient period of time for alkaline lysis of the biomass and formation of an alkaline lysis batch,
   (c) adding a salt component which neutralizes the lysis buffer and forms the salt component of the 2-phase system, and incubating for a sufficient period of time to neutralize the alkaline lysis batch,
   (d) combining a first polyethylene glycol component having a first average molecular weight, a second polyethylene glycol component having a different, second average molecular weight, and the neutralized alkaline lysis batch of (c), and mixing, wherein the polymer component of the 2-phase system comprises the first and second polyethylene glycol components, and
   (e) forming an upper phase containing contaminants and a lower phase containing the plasmid DNA,
   wherein the suspension of the biomass, the addition of the lysis buffer, salt component and polymer component are all carried out in a single reaction vessel without there being an intermediate centrifugation step.

2. The method according to claim 1, wherein the polymer component has an average molecular weight of 600 to 1,000 g/mol.

3. The method according to claim 2 wherein the polymer component comprises 30-50% (w/w) PEG having an average molecular weight of 600 g/mol (PEG 600) and 50-70% (w/w) PEG having an average molecular weight of 1,000 g/mol (PEG 1000).

4. The method according to claim 1, wherein the concentration of the polymer component is chosen such that two phases are formed with the salt component of the 2-phase system, and that the concentration at which the plasmid DNA changes from the lower phase into the upper phase is not exceeded and contaminants remain in the upper phase or in the interphase.

5. The method according to claim 4, wherein the content of polymer component is at least 10% (w/w) and that the concentration at which the plasmid DNA changes from the lower phase into the upper phase is not exceeded and contaminants remain in the upper phase or in the interphase.

6. The method according to claim 1, wherein tripotassium phosphate ($K_3PO_4$), dipotassium hydrogen phosphate ($K_2HPO_4$) and/or potassium dihydrogen phosphate ($KH_2PO_4$) are used as the salt component.

7. The method according to claim 6, wherein the salt component is added in the form of a buffer solution.

8. The method according to claim 7, wherein the buffer solution is $K_2HPO_4/KH_2PO_4$ buffer.

9. The method according to claim 6, wherein the concentration of the salt component is chosen such that two phases are formed with the polymer component of the 2-phase system, and that the concentration of the salt component at which the plasmid DNA changes from the lower phase into the upper phase is not exceeded and contaminants remain in the upper phase or in the interphase.

10. The method according to claim 9, wherein $K_2HPO_4/KH_2PO_4$ are employed in a total concentration of 5-30% (w/w).

11. The method according to either of claim 7 or 10, wherein the buffer system of the salt component has a pH in the range of from pH 5.8 to pH 8.5.

12. The method according to claim 1, wherein the plasmid DNA to be isolated includes plasmids, cosmids and plasmids as well as eukaryotic vectors.

13. The method according to claim 12, wherein the eukaryotic vectors are yeast vectors.

14. The method according to claim 1, wherein the lysis buffer is an alkaline lysis buffer containing sodium dodecyl sulphate (SDS).

15. The method according to claim 14, wherein the reaction vessel is agitated to assist in lysing the biomass.

16. A method for isolating plasmid DNA from a clarified lysate, said method comprising an aqueous 2-phase system having a polymer component and a salt component, said method comprising the steps of:
  (a) adding a salt component which neutralizes the clarified lysate and forms the salt component of the 2-phase system, and incubating for a sufficient period of time to neutralize the clarified lysate,
  (b) combining a first polyethylene glycol component having a first average molecular weight, a second polyethylene glycol component having a different, second average molecular weight, and the neutralized clarified lysate of (a), and mixing, wherein the polymer component of the 2-phase system comprises the first and second polyethylene glycol components, and
  (c) forming an upper phase containing contaminants and a lower phase containing the plasmid DNA,
  wherein the addition of the salt component and polymer component are all carried out in a single reaction vessel without there being an intermediate centrifugation step.

17. The method according to claim 1, wherein the lower phase forming in step (e) from claim 1 is additionally purified from contaminants.

18. The method according to claim 1, further comprising the additional purification steps:
  (f) separating the lower phase forming in step (e) from the upper phase formed in step (e),
  (g) adding the salt component to the separated lower phase from step (f),
  (h) adding the polymer component, and
  (i) mixing of the solution and forming phases.

19. The method according to either claim 1, wherein the plasmid DNA in the lower phase is further isolated and desalinated by ultrafiltration/diafiltration to obtain ultrafiltrated/diafiltrated plasmid DNA.

20. The method according to claim 1, wherein the formation of the phases in step (e) is accelerated by centrifugation.

21. The method according to claim 1, wherein the alkaline lysis batch from step (c) for claim 1 is agitated during and/or after the addition of the salt component.

22. The method according to claim 1, wherein the method is automated.

23. The method according to claim 1, wherein the method is capable of isolating more than 2 grams of plasmid DNA per reaction vessel.

24. The method according to claim 1, wherein the lower phase contains a level of RNA that is not detectable by gel electrophoresis.

25. The method according to claim 1 wherein the polymer component has an average molecular weight of 700-900 g/mol.

26. The method according to claim 1 wherein the polymer component has an average molecular weight of 750-880 g/mol.

27. The method according to claim 1 wherein the polymer component comprises a PEG having an average molecular weight of 1,000 g/mol (PEG 1000).

28. The method according to claim 1 wherein the polymer component comprises a PEG having an average molecular weight of 600 g/mol (PEG 600).

29. The method according to claim 1 wherein the polymer component comprises a PEG having an average molecular weight of 600 g/mol (PEG 600) and a PEG having an average molecular weight of 1,000 g/mol (PEG 1000).

30. The method according to claim 19 wherein the ultrafiltrated/diafiltrated plasmid DNA comprises less open circular plasmid DNA than super-coiled plasmid DNA.

31. The method according to claim 30, wherein the open circular DNA is depleted.

32. The method according to claim 30, wherein the method is performed to preferentially isolate super-coiled plasmid DNA from open circular DNA.

33. The method according to claim 1, wherein the lower phase has been depleted by more than 99% of genomic DNA.

34. The method of claim 1 wherein the lower phase is more than 80% depleted of RNA.

35. The method of claim 1 wherein the lower phase is more than 85% depleted of RNA.

36. The method of claim 1 wherein the lower phase is more than 90% depleted of RNA.

37. The method of claim 1 wherein the lower phase contains a level of genomic DNA that is not detectable by gel electrophoresis.

38. The method of claim 2 wherein the lower phase contains a level of RNA less than the level of RNA in the upper phase.

39. The method of claim 27 wherein the upper phase contains a level of RNA greater than the level of RNA in the lower phase and wherein the upper phase contains a level of plasmid DNA lower than the level of plasmid DNA in the lower phase.

* * * * *